United States Patent
Wlassics et al.

(10) Patent No.: US 10,208,147 B2
(45) Date of Patent: Feb. 19, 2019

(54) FLUOROALLYLSULFONYL AZIDE MONOMERS AND POLYMERS THERE FROM

(71) Applicant: SOLVAY SPECIALTY POLYMERS ITALY S.P.A., Bollate (IT)

(72) Inventors: Ivan Wlassics, Garessio (IT); Vito Tortelli, Milan (IT); Alessio Marrani, Lecco (IT)

(73) Assignee: Solvay Specialty Polymers Italy S.P.A., Bollate (Milan) (IT)

( * ) Notice: Subject to any disclaimer, the term of this patent is extended or adjusted under 35 U.S.C. 154(b) by 20 days.

(21) Appl. No.: 14/365,423

(22) PCT Filed: Dec. 6, 2012

(86) PCT No.: PCT/EP2012/074627
§ 371 (c)(1),
(2) Date: Jun. 13, 2014

(87) PCT Pub. No.: WO2013/087498
PCT Pub. Date: Jun. 20, 2013

(65) Prior Publication Data
US 2014/0329970 A1    Nov. 6, 2014

(30) Foreign Application Priority Data
Dec. 16, 2011  (EP) .................................... 11194148

(51) Int. Cl.
*C07C 311/49* (2006.01)
*C08F 214/22* (2006.01)
(Continued)

(52) U.S. Cl.
CPC ........ *C08F 214/222* (2013.01); *C07C 311/49* (2013.01); *C08F 14/18* (2013.01);
(Continued)

(58) Field of Classification Search
USPC ........................................... 526/250; 525/242
See application file for complete search history.

(56) References Cited

U.S. PATENT DOCUMENTS 4,235,804 A * 11/1980 Krespan .................. B01J 27/12
528/377
4,349,650 A * 9/1982 Krespan ................ C07C 43/225
204/296

(Continued)

FOREIGN PATENT DOCUMENTS

EP          661304 A1    7/1995
EP          860436 A1    8/1998
(Continued)

OTHER PUBLICATIONS

Wlassics I. et al., "Perfluoro Allyl Sulfate (FAFS) : a versatile building block for new fluoroallylic compounds", Molecules, 2011, vol. 16, p. 6512-6540.
(Continued)

*Primary Examiner* — Mark Kaucher
*Assistant Examiner* — Henry Hu (57) ABSTRACT

This invention pertains to fluoroallylsulfonyl azide compounds of formula: $CF_2=CF-CF_2-R_f-SO_2N_3$ formula (I) wherein $R_f$ is a divalent (per)fluorinated group, optionally comprising one or more than one ethereal oxygen atom [monomer (Az)], which are useful as functional monomers in fluoropolymers, to the fluoropolymers which comprise recurring units derived from such fluoroallylsulfonyl azide compounds, to a process for their manufacture, to a curable compound comprising the same and to a method for cross-linking the same.

20 Claims, 1 Drawing Sheet

(51) Int. Cl.
*C08F 14/18* (2006.01)
*C08K 5/00* (2006.01)
*C08K 5/43* (2006.01)

(52) U.S. Cl.
CPC .......... *C08F 214/22* (2013.01); *C08K 5/0025* (2013.01); *C08K 5/43* (2013.01)

(56) References Cited

U.S. PATENT DOCUMENTS

| | | | | |
|---|---|---|---|---|
| 6,365,693 | B1* | 4/2002 | Hung | C07C 311/49 |
| | | | | 526/247 |
| 6,417,379 | B1* | 7/2002 | Hung | C07C 311/49 |
| | | | | 552/5 |
| 7,122,608 | B1 | 10/2006 | Brinati et al. | |
| 2007/0166838 | A1 | 7/2007 | Marsman et al. | |
| 2010/0093878 | A1* | 4/2010 | Yang | C08F 24/00 |
| | | | | 521/27 |
| 2010/0324222 | A1* | 12/2010 | Hung | C08L 27/16 |
| | | | | 525/200 |

FOREIGN PATENT DOCUMENTS

| | | |
|---|---|---|
| WO | 9705122 A1 | 2/1997 |
| WO | 2010021962 A2 | 2/2010 |
| WO | 2010147697 A2 | 12/2010 |
| WO | WO-2010/147697 A2 * | 12/2010 |

OTHER PUBLICATIONS

Krespan C.G. et al., "Perfluoroallylfluorosulfate, a reactive new perfluoroallylating agent", Journal of American Chemical Society, 1981, vol. 103, p. 5598-5599—American Chemical Society.

* cited by examiner

FLUOROALLYLSULFONYL AZIDE MONOMERS AND POLYMERS THERE FROM

CROSS-REFERENCE TO RELATED APPLICATION

This application is a U.S. national stage entry under 35 U.S.C. § 371 of International Application No. PCT/EP2012/074627 filed Dec. 6, 2012, which claims priority to European application No. EP 11194148.0 filed on Dec. 16, 2011. The entire contents of these applications are explicitly incorporated herein by this reference.

TECHNICAL FIELD

This invention pertains to fluoroallylsulfonyl azide compounds which are useful as functional monomers in fluoropolymers, to the fluoropolymers which comprise recurring units derived from such fluoroallylsulfonyl azide compounds, to a process for their manufacture, to a curable compound comprising the same and to a method for cross-linking the same.

BACKGROUND ART

Cross-linking of bulk fluoropolymers, including thermoplasts and elastomers, is one of the most common techniques in polymer science to stabilize shape, improve mechanical properties and fix structure of shaped articles and accordingly many methods have been reported on how to achieve well-defined cross-linking processes.

Within this scenario, sulfonyl azide groups have attracted much attention for being either incorporated as cure-site in polymeric chain or used as coupling agents, because of their peculiar reactivity. Actually, it is well known that sulfonyl azide group decomposes thermally or under UV radiation to form a nitrene intermediate, which is capable of extracting a hydrogen atom or inserting into a saturated carbon-hydrogen bond or coupling with another nitrene moiety to form a diazo compound.

Chemistry of azide groups, and more particularly of sulfonazide groups, has thus found application in the domain of fluoropolymers for effecting crosslinking of the same. Thus, WO 2010/021962 (3M INNOVATIVE PROPERTIES CO) 25 Feb. 2010 discloses fluoropolymers comprising azide groups (different from sulfonazide moieties) which are generally present as end-groups and which can be introduced in the fluoropolymer as a result of the use of an azide compound as radical initiator, using an azide group-containing chain transfer agent or by nucleophilic deplacement of leaving groups present in the polymer by use of azides.

Also, US 2007166838 (KONINKL PHILIPS ELECTRONICS NV) 19 Jul. 2007 discloses, inter alia, crosslinkable polymer compositions comprising a VDF-TrFE polymer and, among others crosslinking agents, an azide compound, e.g. 4,4-dithiobisphenyl-azide, 3,3'-diazododiphenyl sulphone.

Further, in addition, sulfonyl azide-containing molecules are otherwise recognized as quite robust compounds, e.g. stable in usual polymerization conditions, including in aqueous media, so that monomers carrying such moieties have already been used in standard free radical polymerization processes.

Sulfonyl azide-containing monomers have been already incorporated in fluoropolymers. Thus, U.S. Pat. No. 6,365,693 (DUPONT DOW ELASTOMERS LLC) 2 Apr. 2002 discloses fluoroalkanesulfonylazide unsaturated compounds which can be used as functional monomers in fluoropolymers, in particular in fluoroelastomers, including VDF-based fluoroelastomers. These compounds comply with formula $CF_2=CF-(O)_p-R_f-(CH_2)_n-S(O)_qN_3$, wherein p=0 or 1; n=0-4; q=1 or 2; and $R_f$ is a $C_1$-$C_{16}$ perfluoroalkyl of perfluoroalkoxy group. Embodiments with p=1, i.e. perfluorovinylethers derivatives are specifically disclosed: $CF_2=CF-O-CF_2-CF(CF_3)-O-CF_2CF_2-SO_2N_3$, $CF_2=CF-O-CF_2CF_2-SO_2N_3$, $CF_2=CF-O-CF_2CF_2CF_2-SO_2N_3$, $CF_2=CF-O-CF_2CF_2CF_2CF_2-SO_2N_3$. Other embodiments disclosed are those wherein p=0 and an oxygen atom is comprised in the $R_f$ moiety, including notably compound: $CF_2=CF-CF_2CF_2-O-CF_2CF_2-SO_2N_3$.

Similarly, WO 2010/147697 (DUPONT PERFORMANCE ELASTOMERS) 23 Dec. 2010 discloses certain curable compositions based on fluoroelastomer containing azide groups, including through the incorporation of recurring units comprising azide groups; as per the description of azide-containing monomers, this document refers back to document U.S. Pat. No. 6,365,693 (DUPONT DOW ELASTOMERS LLC) 2 Apr. 2002 and mentions perfluorinated vinyl ether compounds, including notably $CF_2=CF-O-CF_2-CF(CF_3)-O-CF_2CF_2-SO_2N_3$, $CF_2=CF-O-CF_2CF_2-SO_2N_3$, $CF_2=CF-O-CF_2CF_2CF_2-SO_2N_3$, $CF_2=CF-O-CF_2CF_2CF_2CF_2-SO_2N_3$.

Nevertheless, the chemistry and incorporation of these monomers wherein the ethylenically unsaturated moiety is of formula $CF_2=CF-O-$ is strongly influenced by this vinyl ether character, so that effectiveness in incorporation in the fluoropolymer chain by radical addition over transfer and beta-scission phenomena, and chain transfer phenomena, monomer distribution and molecular weight in copolymers comprising the same and cross-linking ability thereof might be negatively affected.

SUMMARY OF INVENTION

The Applicant has now found a new class of sulfonyl azide containing monomers which have improved reactivity in incorporation in fluoropolymers and which are able to provide fluoropolymers of increased molecular weight and which are easy to be crosslinked, even at low monomer concentration.

The invention thus pertains to sulfonyl azide allylic monomers of formula:

$$CF_2=CF-CF_2-O-R_f-SO_2N_3 \qquad \text{formula (I)}$$

wherein $R_f$ is a divalent (per)fluorinated group, optionally comprising one or more than one ethereal oxygen atom [monomer (Az)].

These monomers (Az) have been found to easily react with additional monomers under radical polymerization conditions, so as to provide polymers having high molecular weight and possessing outstanding curing behaviour.

The group $R_f$ is preferably a group of formula $-CF_2-R_f'-$, with the $-CF_2-$group being bound to the ethereal oxygen depicted in formula (I) and the $R_f'$ group being bound to the sulfonazide group, as depicted in formula (Ia):

$$CF_2=CF-CF_2-O-CF_2-R_f'-SO_2N_3 \quad \text{formula (Ia),}$$

wherein $R_f'$ is a divalent $C_1$-$C_{12}$ (per)fluorinated group, optionally comprising one or more than one ethereal oxygen atom.

Most preferably, monomer (Az) complies with formula (Ib) herein below:

$$CF_2=CF-CF_2-O-CF_2-CF_2-SO_2N_3 \quad \text{formula (Ib).}$$

The invention further pertains to a process for the manufacture of said monomer (Az).

The monomer (Az) can be prepared by reaction of a fluorosulfonic precursor of formula (II):

$$CF_2=CF-CF_2-O-R_f-SO_2F \quad \text{formula (II)}$$

wherein $R_f$ is a divalent (per)fluorinated group, optionally comprising one or more than one ethereal oxygen atom, with an azide salt [salt (Az)].

The salt (Az) is preferably selected from the group consisting of alkali metal azides, alkaline earth metal azides, and ammonium azides of formula $N(R_H)_4N_3$ wherein each of $R_H$, equal or different from each other and at each occurrence, is hydrogen or an optionally substituted $C_1$-$C_{20}$ alkyl group, which can be, where possible, linear, branched or cyclic.

The reaction between the fluorosulfonic derivative and the salt (Az) is generally carried out at a temperature of 0 to 60° C., preferably of 10 to 50° C., most preferably of from about 15 to about 40° C.

Typically this reaction is carried out in the presence of a solvent. The choice of the solvent is not particularly critical; a polar protic or aprotic solvent can be used; further, an aqueous medium can be equally employed.

It is generally understood that when an aqueous medium is used, the salt (Az) as above detailed will be soluble in the aqueous phase, while the precursor (II), as above detailed, will generally present in a separated organic phase. Thus, when an aqueous medium is used, a phase transfer catalyst is generally added in the reaction mixture.

The choice of the phase transfer catalyst is not particularly critical; long chain quaternary ammonium salts can be used. A phase transfer catalyst which has been found particularly useful is $CH_3-N-[(CH_2)_7CH_3]_3^+Cl^-$, commercialized under the name Aliquat.

For obtaining preferred monomers (Az) of formula (Ia), a sulfonic precursor of formula (IIa):

$$CF_2=CF-CF_2-O-CF_2-R_f'-SO_2F \quad \text{formula (IIa),}$$

wherein $R_f'$ is a divalent $C_1$-$C_{12}$ (per)fluorinated group, optionally comprising one or more than one ethereal oxygen atom,
is reacted with an azide salt [salt (Az)], as above detailed.

Compounds of formula (IIa) can be obtained by reacting fluoroallylfluorosulfate with a fluoroacyl compound of formula $FO_2S-Rf'-COF$, in the presence of a fluoride salt [salt (F)], as notably sketched in scheme herein below:

This reactivity is notably described in WLASSICS, I., et al. Perfluoro Allyl Sulfate (FAFS): a Versatile Building Block For New Fluoroallylic Compounds. *Molecules*. 2011, vol. 16, p. 6512_6540.

Fluoroallylfluorosulfate (FAFS) is an easily available fluorinated intermediate, which can be prepared in high yield notably via treatment of hexafluoropropylene with sulphur trioxide in the presence of boron-based catalysts, as disclosed in U.S. Pat. No. 4,235,804 (E.I. DUPONT DE NEMOURS) 25 Nov. 1980 and KRESPAN, G., et al. Perfluoroallylfluorosulfate, a reactive new perfluoroallylating agent. *J. Am. Chem. Soc.* 1981, vol. 103, p. 5598-5599.

The process for manufacturing the compounds of formula (Ia) thus advantageously comprises reacting fluoroallylfluorosulfate of formula $F-SO_2-O-CF_2-CF=CF_2$ (FAFS) with a salt (F), for yielding a compound of formula (IIa), as above detailed, and then reacting said compound (IIa) with a salt (Az), as above detailed.

The salt (F) is selected from the group consisting of:
fluorides of formula MF, wherein M is selected from the group consisting of alkali metals, Ag, and $N(R'_H)_4$ wherein each of $R'_H$, equal or different from each other and at each occurrence, is hydrogen or an optionally substituted $C_1$-$C_{20}$ alkyl group, which can be, where possible, linear, branched or cyclic; and
fluorides of formula $M'F_2$, wherein M' is an alkali earth metal.

Preferred salts (F) are CsF, KF, RbF, LiF, NaF, $CaF_2$, $BaF_2$, $MgF_2$, $SrF_2$, AgF. Most preferred salts (F) are CsF and KF.

Still, the invention pertains to a fluoropolymer [polymer (F)] comprising recurring units derived from at least one monomer (Az), as above defined, and, optionally, recurring units derived from at least one ethylenically unsaturated fluorinated monomer [monomer (F)] different from monomer (Az) and/or recurring units derived from an ethylenically unsaturated non-fluorinated monomer [monomer (H)].

Polymer (F) typically comprises recurring units derived from monomer (Az) in an amount of at least 0.01, preferably at least 0.05, more preferably at least 0.1% moles, with respect to the total moles of recurring units of polymer (F).

It is generally understood that when the monomer (Az) is present in polymer (F) in an amount of less than 0.01% moles, as above detailed, the crosslinking reactivity might be slower.

While the upper amount of monomer (Az) is not particularly limited, to the aim of obtaining curable polymers (F) having good curing behaviour, it is generally preferred to limit the amount of recurring units derived from monomer (Az) to less than 20% moles, preferably of less than 10% moles, with respect to the total moles of recurring units of polymer (F).

The expression 'fluorinated monomer' is used herein according to its usual meaning, i.e. to designate a monomer comprising at least one fluorine atom.

Similarly, the expression 'non-fluorinated monomer' is used herein according to its usual meaning, i.e. to designate a monomer which is free from fluorine atom(s).

Monomers (H) that can be used in the copolymers of this invention include: ethylene, propylene, n-butylene, iso-butylene, vinyl acetate (VAc), and vinyl ethers such as methyl vinyl ether.

The polymer (F) of this invention may be glassy, thermoplastic or elastomeric. They may be amorphous or partially crystalline, melt-fabricable or non-melt-fabricable. One skilled in the art will readily recognize that such polymer properties are controlled by the type of monomers used in the copolymer and their relative levels.

Generally, polymer (F) will comprises recurring units derived from at least one monomer (Az), as above detailed, and recurring units derived from at least one fluorinated monomer [monomer (F)].

The monomer (F) is generally selected from the group consisting of:
- $C_2$-$C_8$ perfluoroolefins, such as tetrafluoroethylene, and hexafluoropropene;
- $C_2$-$C_8$ hydrogenated fluoroolefins, such as vinyl fluoride, 1,2-difluoroethylene, vinylidene fluoride and trifluoroethylene;
- perfluoroalkylethylenes complying with formula $CH_2=CH-R_{f0}$, in which $R_{f0}$ is a $C_1$-$C_6$ perfluoroalkyl;
- chloro- and/or bromo- and/or iodo-$C_2$-$C_6$ fluoroolefins, like chlorotrifluoroethylene;
- (per)fluoroalkylvinylethers complying with formula $CF_2=CFOR_{f1}$ in which $R_{f1}$ is a $C_1$-$C_6$ fluoro- or perfluoroalkyl, e.g. $CF_3$, $C_2F_5$, $C_3F_7$;
- $CF_2=CFOX_0$ (per)fluoro-oxyalkylvinylethers, in which $X_0$ is a $C_1$-$C_{12}$ alkyl, or a $C_1$-$C_{12}$ oxyalkyl, or a $C_1$-$C_{12}$ (per)fluorooxyalkyl having one or more ether groups, like perfluoro-2-propoxy-propyl;
- (per)fluoroalkylvinylethers complying with formula $CF_2=CFOCF_2OR_{f2}$ in which $R_{f2}$ is a $C_1$-$C_6$ fluoro- or perfluoroalkyl, e.g. $CF_3$, $C_2F_5$, $C_3F_7$ or a $C_1$-$C_6$ (per)fluorooxyalkyl having one or more ether groups, like $-C_2F_5-O-CF_3$;
- functional (per)fluoro-oxyalkylvinylethers complying with formula $CF_2=CFOY_0$, in which $Y_0$ is a $C_1$-$C_{12}$ alkyl or (per)fluoroalkyl, or a $C_1$-$C_{12}$ oxyalkyl, or a $C_1$-$C_{12}$ (per)fluorooxyalkyl having one or more ether groups and $Y_0$ comprising a carboxylic or sulfonic acid group, in its acid, acid halide or salt form;
- fluorodioxoles, of formula (I):

wherein each of $R_{f3}$, $R_{f4}$, $R_{f5}$, $R_{f6}$, equal or different each other, is independently a fluorine atom, a $C_1$-$C_6$ fluoro- or per(halo)fluoroalkyl, optionally comprising one or more oxygen atom, e.g. $-CF_3$, $-C_2F_5$, $-C_3F_7$, $-OCF_3$, $-OCF_2CF_2OCF_3$.

The polymer (F) might comprise recurring units derived from one or from more than one monomers (F), as above detailed.

According to a preferred embodiment, the polymer (F) comprises recurring units derived from at least one monomer (Az), as above detailed, and recurring units derived from vinylidene fluoride (VDF).

The polymers (F) according to this embodiment will be designated herein below as polymers (VDF).

Polymers (VDF) generally comprise at least 10, preferably at least 20, more preferably at least 40% moles of recurring units derived from VDF, with respect to the total moles of recurring units of polymer (VDF).

Polymers (VDF) generally comprise at most 90, preferably at most 80, more preferably at most 60% moles of recurring units derived from VDF, with respect to the total moles of recurring units of polymer (VDF).

Preferably, polymer (VDF) according to this preferred embodiment comprises at least one monomer (Az), as above detailed, and recurring units derived from vinylidene fluoride (VDF) and from trifluoroethylene (TrFE).

The Applicant has found that the incorporation of monomer (Az) in the VDF-TrFE polymers of this embodiment provides not only the above mentioned advantages of yielding high molecular weight materials with outstanding curing capabilities, but also enables maintaining suitable piezo-, ferro-, pyro-electric behaviour typical of VDF-TrFE copolymers.

Said preferred polymer (VDF) generally comprises 10 to 50% by moles preferably from 15 to 40% moles of recurring units derived from TrFE.

Preferred polymer (VDF) of the invention may further comprise recurring units derived from one or more than one monomer (F) other than VDF and TrFE, such as notably hexafluoropropylene, tetrafluoroethylene, chlorotrifluoroethylene.

Nevertheless, polymers (VDF) consisting essentially of recurring units derived from monomer (Az), VDF and TrFE are generally preferred.

Such most preferred polymers (VDF) typically consists essentially of:
- from 0.01 to 10% by moles, preferably from 0.05 to 10% by moles of recurring units derived from monomer (Az), as above detailed;
- from 10 to 50% by moles, preferably from 15 to 40% moles of recurring units derived from TrFE; and
- from 50 to 90% moles, preferably from 60 to 85% moles of recurring units derived from VDF, with respect to the total moles of recurring units of polymer (VDF).

Another aspect of the invention pertains to a process for the manufacture of [polymer (F)], as above detailed.

Polymer (F) can be manufactured according to standard techniques.

The process for manufacturing polymer (F) generally comprises polymerizing in the presence of a radical initiator at least one monomer (Az), as above detailed, and optionally, at least one ethylenically unsaturated fluorinated monomer [monomer (F)] different from monomer (Az) and/or at least one ethylenically unsaturated non-fluorinated monomer [monomer (H)].

Said process may be carried out at a temperature between 10 to 150° C., preferably 20° C. to 120° C.

The pressure is typically between 2 and 100 bar, in particular 5 to 50 bar.

As is likewise well known in the art, dispersion, emulsion, solution or suspension processes may be employed, and the processes may be conducted on a continuous, batch or semi-batch basis.

The process can be preferably carried out in an aqueous medium or in a solvent.

Generally, aqueous polymerization media will be preferred.

In case of aqueous polymerization media, polymerization can be carried out in emulsion or in suspension, with aqueous emulsion polymerization being preferred.

Aqueous emulsion polymerization process will generally require the presence of a suitable emulsifying agent, which can be notably selected from fluorinated or non-fluorinated surfactants, preferably fluorinated surfactants [surfactant (FS)].

The surfactant (FS) complies advantageously with formula:

wherein $R_{fS}$ is a $C_5$-$C_{16}$ (per)fluoroalkyl chain or a (per)fluoro(poly)oxyalkyl chain interrupted by one or more ethereal oxygen atoms, $X^-$ is —COO$^-$, —PO$_3^-$ or —SO$_3^-$, $M^+$ is selected from $H^+$, $NH_4^+$, an alkaline metal ion and j can be 1 or 2.

The pH of the polymerization media may be in the range of pH 2-11, preferably 3-10, most preferably 4-10.

Organic radical initiators can be used and include, but are not limited to, the following: acetylcyclohexanesulfonyl peroxide; diacetylperoxydicarbonate; dialkylperoxydicarbonates such as diethylperoxydicarbonate, dicyclohexylperoxydicarbonate, di-2-ethylhexylperoxydicarbonate; tert-butylperneodecanoate; 2,2'-azobis(4-methoxy-2,4-dimethylvaleronitrile); tert-butylperpivalate; dioctanoylperoxide; dilauroyl-peroxide; 2,2'-azobis(2,4-dimethylvaleronitrile); tert-butylazo-2-cyanobutane; dibenzoylperoxide; tert-butyl-per-2-ethylhexanoate; tert-butylpermaleate; 2,2'-azobis(isobutyronitrile); bis(tert-butylperoxy)cyclohexane; tert-butyl-peroxyisopropylcarbonate; tert-butylperacetate; 2,2'-bis(tert-butylperoxy)butane; dicumyl peroxide; di-tert-amyl peroxide; di-tert-butyl peroxide; p-methane hydroperoxide; pinane hydroperoxide; cumene hydroperoxide; and tert-butyl hydroperoxide. Other suitable initiators include halogenated free radical initiators such as chlorocarbon based and fluorocarbon based acyl peroxides such as trichloroacetyl peroxide, bis(perfluoro-2-propoxy propionyl) peroxide, [CF$_3$CF$_2$CF$_2$OCF(CF$_3$)COO]$_2$, perfluoropropionyl peroxides, (CF$_3$CF$_2$CF$_2$COO)$_2$, (CF$_3$CF$_2$COO)$_2$, {(CF$_3$CF$_2$CF$_2$)—[CF(CF$_3$)CF$_2$O]$_m$—CF(CF$_3$)—COO}$_2$ where m=0-8, [ClCF$_2$(CF$_2$)$_n$COO]$_2$, and [HCF$_2$(CF$_2$)$_n$COO]$_2$ where n=0-8; perfluoroalkyl azo compounds such as perfluoroazoisopropane, [(CF$_3$)$_2$CFN=]$_2$, R R$^\square$ N=NRR$^\square$, where RR$^\square$ is a linear or branched perfluorocarbon group having 1-8 carbons; stable or hindered perfluoroalkane radicals such as hexafluoropropylene trimer radical, [(CF$_3$)$_2$CF]$_2$(CF$_2$CF$_2$)C$^\bullet$ radical and perfluoroalkanes.

Redox systems, comprising at least two components forming a redox couple, such as dimethylaniline-benzoyl peroxide, diethylaniline-benzoyl peroxide and diphenylamine-benzoyl peroxide can also be used to initiate the polymerization.

Also, inorganic radical initiators can be used and include, but are not limited to, the followings: persulfates, like sodium, potassium or ammonium persulfates, permanganates, like potassium permanganate.

Organic radical initiators, as those above detailed, are preferred. Among them, the peroxides having a self-accelerating decomposition temperature (SADT) higher than 50° C., are particularly preferred, such as for instance: diterbutylperoxide (DTBP), diterbutylperoxyisopropylcarbonate, terbutyl(2-ethyl-hexyl)peroxycarbonate, terbutylperoxy-3,5,5-trimethyl hexanoate.

The radical initiator is advantageously included in a concentration ranging from 0.001 to 20 percent by weight of the polymerization medium.

Polymerization can be carried out in the presence of a chain transfer agent.

If required, a chain transfer agent can be used; this latter is selected from those known in the polymerization of fluorinated monomers, such as for instance: ketones, esters, ethers or aliphatic alcohols having from 3 to 10 carbon atoms, such as acetone, ethylacetate, diethylether, methyl-tert-butyl ether, isopropyl alcohol, etc.; chloro(fluoro)carbons, optionally containing hydrogen, having from 1 to 6 carbon atoms, such as chloroform, trichlorofluoromethane; bis(alkyl)carbonates wherein the alkyl has from 1 to 5 carbon atoms, such as bis(ethyl)carbonate, bis(isobutyl) carbonate. The chain transfer agent can be fed to the polymerization medium at the beginning, continuously or in discrete amounts (step-wise) during the polymerization, continuous or stepwise feeding being preferred.

The polymer (F) emerging from the reactor may be isolated and dried by any known technique, taking care that the polymer is not heated enough to cause crosslinking. Alternatively, an aqueous dispersion emerging from the reactor may be used directly as-is, for example as a coating composition, or it may first be stabilized by addition of surfactant and/or concentrated by processes well known in the art for the preparation of latex coating compositions.

Polymers (F) of this invention may be mixed with other ingredients, and the resulting crosslinkable composition [composition (CC)], which is another object of the present invention, can submitted to crosslinking to yield a cured article.

The crosslinkable composition comprising the polymer (F) as above detailed will generally comprise at least one curing agent. While polymer (F) may undergo self-crosslinking, i.e. can be cured in the absence of any additional co-agent, it is generally preferred to use a curing agent.

Curing agents, when used in combination with polymer (F) in the crosslinking process of the invention, are used in amounts generally of between 0.5% and 10% and preferably between 1% and 7% by weight relative to the polymer (F).

Among these curing agents, the following are commonly used:
polyallyl derivatives comprising more than one ethylenically unsaturated allylic double bond, including triallyl cyanurate; triallyl isocyanurate (TAIC); tris(diallylamine)-s-triazine; triallyl phosphite; N,N-diallylacrylamide; N,N,N',N'-tetraallylmalonamide;
polyvinyl derivatives comprising more than one ethylenically unsaturated vinyl double bond, including trivinyl isocyanurate; 2,4,6-trivinyl methyltrisiloxane;
bis-olefin [bis-olefin (OF)] having general formula:

wherein $R_1$, $R_2$, $R_3$, $R_4$, $R_5$ and $R_6$, equal or different from each other, are H or $C_1$-$C_5$ alkyl; Z is a group of formula —(O)$_{e1}$-E-(O)$_{e2}$—, wherein e1 and e2, equal to or different from each other are independently 1 or 0, and E is a divalent $C_1$-$C_{18}$ group, optionally containing oxygen atoms, preferably at least partially fluorinated, like notably a (per)fluoropolyoxyalkylene radical, e.g. as described in EP 661304 A (AUSIMONT SPA) 7 Jul. 1995;
triazines substituted with ethylenically unsaturated groups, such as notably those described in EP 860436 A (AUSIMONT SPA) 26 Aug. 1998 and WO 97/05122 (DU PONT) 13 Feb. 1997;
polyazides compounds comprising more than one azide groups, including notably diazides of formula:

wherein each of j an j', equal to or different from each other, is 0 or an integer of 1 to 3, provided that j+j' is of at least 2, each of sd and sd', equal to or different from each other is independently 0 or 1, each of qd and qd', equal to or different from each other is independently 1 or 2, and $J_d$ is a (hydro)(fluoro)carbon group, optionally containing oxygen atoms, preferably at least partially fluorinated [agent (Cz)].

The bis-olefin (OF) is preferably selected from the group consisting of those complying with formulae (OF-1), (OF-2) and (OF-3):

(OF-1)

wherein j is an integer between 2 and 10, preferably between 4 and 8, and R1, R2, R3, R4, equal or different from each other, are H, F or $C_{1-5}$ alkyl or (per)fluoroalkyl group;

(OF-2)

wherein each of A, equal or different from each other and at each occurrence, is independently selected from F, Cl, and H; each of B, equal or different from each other and at each occurrence, is independently selected from F, Cl, H and $OR_B$, wherein $R_B$ is a branched or straight chain alkyl radical which can be partially, substantially or completely fluorinated or chlorinated; E is a divalent group having 2 to 10 carbon atom, optionally fluorinated, which may be inserted with ether linkages; preferably E is a —$(CF_2)_m$— group, with m being an integer from 3 to 5; a preferred bis-olefin of (OF-2) type is $F_2C$=CF—O—$(CF_2)_5$—O—CF=$CF_2$.

(OF-3)

wherein E, A and B have the same meaning as above defined; R5, R6, R7, equal or different from each other, are H, F or $C_{1-5}$ alkyl or (per)fluoroalkyl group.

The agent (Cz) is preferably a fluorinated polyazide of formula:

formula (A)

wherein each of g1 and g2, equal to or different from each other, is 1 or 2, each of s1 and s2, equal to or different from each other, is 0 or 1, each of na and na' is independently zero or an integer of 1 to 3, provided that the sum na+na' is at least 2, each of $R_H$ and $R'_H$, equal to or different from each other, is a $C_1$-$C_{12}$ hydrocarbon group free of fluorine atoms, nh and nh', equal or different from each other are independently 0 or 1, and $R_f$ is selected from the group consisting of i) a $C_3$-$C_{20}$ fluorocarbon group, possibly comprising one or more ethereal oxygen atoms, ii) an oligomer comprising copolymerized units of vinylidene fluoride and trifluoroethylene.

According to a first embodiment, the agent (Cz) advantageously complies with formula (B) herein below:

formula (B)

wherein each of m and m' is independently an integer of 1 to 6, and RBf is a $C_3$-$C_{10}$ fluorocarbon group, possibly comprising one or more ethereal oxygen atoms.

The agent (Cz) of this first embodiment complies preferably with formula (C) herein below:

formula (C)

wherein each of m and m' is independently an integer of 1 to 6, preferably m and m'=2, and nc is an integer of 4 to 10, preferably of 4 to 8.

Non limitative examples of agent (Cz) according to this variant are notably those of formula: $N_3$—$(CH_2)_2$—$(CF_2)_2$—$(CH_2)_2$—$N_3$, $N_3$—$(CH_2)_2$—$(CF_2)_4$—$(CH_2)_2$—$N_3$, $N_3$—$(CH_2)_2$—$(CF_2)_6$—$(CH_2)_2$—$N_3$, $N_3$—$(CH_2)_2$—$(CF_2)_8$—$(CH_2)_2$—$N_3$, $N_3$—$(CH_2)_2$—$(CF_2)_{10}$—$(CH_2)_2$—$N_3$.

Compounds of formula (C) can be manufactured by telomerisation of tetrafluoroethylene in the presence of iodine, followed by ethylene addition/incorporation onto C—I bonds, and subsequent nucleophilic displacement of iodine by an azide salt, preferably $NaN_3$.

According to a second embodiment, the agent (Cz) advantageously complies with formula (D) herein below:

formula (D)

wherein each of g1 and g2, equal to or different from each other, is 1 or 2, and $R^D_f$ is a $C_3$-$C_{20}$ fluoroalkyl group, possibly comprising one or more ethereal oxygen atoms.

Preferably, the agent (Cz) of this second embodiment complies with formula (E) herein below:

formula (D)

wherein $R^E_f$ is a $C_3$-$C_{20}$ fluoroalkyl group, possibly comprising one or more ethereal oxygen atoms.

Non limitative examples of agent (Cz) according to this variant are notably those of formula: $N_3SO_2$—$C_4F_8$—$SO_2N_3$, $N_3SO_2$—$(CF_2)_2$—O—$C_4F_8$—O—$(CF_2)_2$—$SO_2N_3$, $N_3SO_2$—$(CF_2)_2$—O—$CF(CF_3)CF_2O$—$C_4F_8$—O—$CF_2$—$CF(CF_3)O$—$(CF_2)_2$—$SO_2N_3$, $N_3SO_2$—$(CF_2)_2$—O—$CF_2CF(CF_3)O$—$C_4F_8$—O—$CF_2$—$CF(CF_3)O$—$(CF_2)_2$—$SO_2N_3$, $N_3SO_2$—$(CF_2)_2$—O—$CF_2CF(CF_3)O$—$C_4F_8$—O—$CF(CF_3)$—$CF_2O$—$(CF_2)_2$—$SO_2N_3$. Group of formula —O—$C_4F_8$—O— in each of the above can be any of —O—$(CF_2CF_2)_2$—O—, —O—$CF_2CF_2$—$CF(CF_3)$—O—, —O—$CF(CF_3)$—$CF(CF_3)$—O—.

Compounds of formula (E) can be manufactured by fluorine assisted dimerization of sulfonyl monomers, e.g. of formulae $CF_2$=CF—$SO_2F$, $CF_2$=CF—O—$CF_2CF_2SO_2F$, $CF_2$=CF—O—$CF(CF_3)CF_2OCF_2CF_2SO_2F$, $CF_2$=CF—O—$CF_2CF(CF_3)OCF_2CF_2SO_2F$, followed by nucleophilic displacement at the fluorosulfonyl group by reaction with an azide salt.

Among above mentioned curing coagents, bis-azides, TAIC, agents (Cz) and bis-olefins (OF), as above detailed, and more specifically those of formula (OF-1), as above detailed, have been found to provide particularly good results; most preferably, agents (Cz) have been found to provide particularly good results.

The polymers (F) of this invention may also be mixed in the composition (CC) with other additives, processing aids and fillers well known in the rubber and plastics industries such as, but not limited to, carbon black, mineral fillers including barium sulfate, talc and silica, fibrillating or non-fibrillating thermoplastic fluoropolymers free from monomer (Az), metal oxides, metal hydroxides and the like.

Still, a method of crosslinking the polymer (F) and/or the composition (CC) as above detailed, for yielding a cured article is another embodiment of the present invention.

Crosslinking of polymer (F) and/or of the composition (CC) of this invention may comprise exposing polymer (F) to UV radiation and/or to heat.

Preferably, crosslinking comprises exposing polymer (F) and/or of the composition (CC) to UV radiation.

The term UV radiation is intended to denote, to the purpose of the invention, electromagnetic radiation with a wavelength shorter than that of visible light, but longer than soft X-rays. It can be subdivided into near UV (380-200 nm wavelength; abbreviation: NUV), far or vacuum UV (200-10 nm; abbreviation: FUV or VUV), and extreme UV (1-31 nm; abbreviation: EUV or XUV). NUV having wavelength from 200 to 380 nm is preferred in the process of the invention. Either monochromatic or polychromatic radiation can be used.

UV radiation can be provided in the crosslinking process of the invention by any suitable UV radiation source. Preferred UV radiation source for the process of the invention is mercury lighting. It is known that a significant portion of the energy radiated from excited mercury vapours is in the ultra-violet part of the spectrum. In the case of the low pressure discharge, more than half of the total energy supplied is radiated in the short-wave UV region at 253.7 nm. High pressure lamps radiate about 10% of their energy in the long-wave UV region at 365.0 nm, but an appreciable amount is also radiated at shorter wavelengths.

The crosslinking process of the present invention can be used for manufacturing whichever kind of cured articles. Parts of electronic devices are more preferably manufactured by such a process, in particular when polymer (F) comprises recurring units derived from VDF and TrFE.

The cured articles can be notably sheets and films, including thin films and nano-layers and/or assemblies of the same.

The cured articles of the invention can be useful notably in different electronic devices including transducers, sensors, actuators, ferroelectric memories, capacitors powdered by electrical devices.

A further object of the present invention is a method for manufacturing one of electrical and electronic devices, comprising using a polymer (F), as above detailed.

Such method generally comprises processing the polymer (F) and/or composition (CC) and crosslinking the same.

Processing can be effected by any known techniques; nevertheless, solution processing techniques, including ink printing, casting, lithographic processes and the like would be preferred.

Crosslinking polymer (F) and/or composition (CC) can be performed as above specified.

The crosslinked polymer (F) of the invention is generally comprised in said devices under the form of bidimensional parts such as films (including thin films, and nano-layers) and sheets, or three-dimensional assemblies of the same.

The parts made of the crosslinked polymer (F) as above detailed are generally comprised as ferroelectric, piezoelectric, pyroelectric or dielectric materials in said electrical and electronic devices.

Should the disclosure of any patents, patent applications, and publications which are incorporated herein by reference conflict with the description of the present application to the extent that it may render a term unclear, the present description shall take precedence.

The invention will be now explained in more details with reference to the following examples, whose purpose is merely illustrative and not intended to limit the scope of the invention.

Preparative Example 1 of Comparison—Synthesis of $CF_2=CFOCF_2CF_2SO_2N_3$ [Monomer (Az1)]

According to a procedure similar to the procedures disclosed in U.S. Pat. No. 6,365,693 (DUPONT DOW ELASTOMERS LLC) 2 Apr. 2002 and modified, as below detailed, the above referenced compound was synthesized. In a three necked round bottomed glass flask 1.375 g=21.15 mmoles of $NaN_3$ were suspended in 13 ml of $CH_3CN$, which has been previously dried by distillation over $P_2O_5$ and storage onto 3A molecular sieves. The mixture was stirred at 500 rpm at 20° C. for about 20 minutes; 5.05 g=18.03 mmoles of $CF_2=CFOCF_2CF_2SO_2F$ (VEFS) were then added dropwise during 19 min. The molar concentration of VEFS ($[CF_2=CFOCF_2CF_2SO_2F]$) in the mixture was thus equal to 1.38 M. The exothermic reaction gave rise to a temperature increase of about 2° C. The reaction mixture, at the end of the addition was found to be milky and became translucent. The mixture was kept under stirring at 20° C. for 48 hours under inert $N_2$ atmosphere. The reaction was brought to completion by heating the mixture for 3 hours at 40° C. The mixture was then cooled at 20° C., and this temperature was then maintained for additional 3 hours. The raw reaction mixture appeared to be an opalescent solution with no visible precipitate. This mixture was poured in 70 ml of distilled water, from which clear and transparent oil having a acre smelling immediately separated.

From quantitative $^{19}F$-NMR determinations, the so precipitated oil was found to correspond to the target product. Aqueous phases were separated and found to contain NaF as reaction by-product.

Yield=57% with respect to the starting amount of VEFS.
Selectivity towards $^{a,b}CF_2=^cCFO^dCF_2{}^eCF_2SO_2N_3$=78% moles.

Remaining 22% moles was found to correspond to $N_3{}^fCF_2{}^gCFHO^hCF_2{}^iCF_2SO_2N_3$.

$^{19}F$-NMR; ($CDCl_3$; ppm): a: −110; b: −118; c: −133; d: −80.2; e: −110.4; f: −90; g: −142 ($J^1_{H,F}$=47 hz); h: −78→−83; i: −110.4

FT-IR (KBr; $cm^{-1}$): 1839 ($CF_2=CFO$— st.); 2156 (—$N_3$ st.); 1421+1463 (—$SO_2$—$N_3$ st.); 1200-1100 (CF st.).

Preparative Example 2—Synthesis of $CF_2=CFCF_2OCF_2CF_2SO_2N_3$ [Monomer (Az2)]

The precursor $FSO_2CF_2CF_2OCF_2CF=CF_2$ was prepared according to methods described in the literature (WLASSICS, I., et al. Perfluoro Allyl Sulfate (FAFS): a Versatile Building Block For New Fluoroallylic Compounds. *Molecules*. 2011, vol. 16, p. 6512_6540.).

Synthetic procedure described above for comparative azide compound (I) was modified so as to ensure minimizing contact between the allylether and the NaF (which is a by product of the reaction) and which could catalyze decomposition of vinyl ether precursor to perfluoropropylene and $FO_2S$—$CF_2$—COF.

In a glass cylindrical jacketed reactor, with three inlets, 15.15 mmoles=5.00 g of $FSO_2CF_2CF_2OCF_2CF=CF_2$ were introduced, in combination with 90 μl of a phase transfer agent commercially available as Aliquat (CH$_3$—N—[(CH$_2$)$_7$CH$_3$]$_3$$^+$Cl$^-$), corresponding to 1% v/v. The solution so obtained was cooled at 15° C. using a cryostat connected to the reactor racket. Using an automatic dispensing syringe containing a solution made of 7.5 ml of distilled H$_2$O and 2.395 g=36.85 mmoles of NaN$_3$, said solution was added dropwise at a rate of 0.1 eq. NaN$_3$/h; reactor temperature was kept at 15° C. during the whole addition time (about 24 hours). Temperature was then raised to 20° C. for further 8 hours. At the end of the reaction, the reaction mixture was composed of two phases. Upper phase, composed of H$_2$O, NaF and residual NaN$_3$ was discarded. Lower phase was recovered and centrifuged at 15° C. and 4000 rpm during 20 minutes so as to eliminate solid particulate residues. A colorless and clear oil was obtained having a characteristic acre smell.

Yield (after purification and separation)=65% moles.
Selectivity=55/45  A/B—A=$^{a,b}$CF$_2$=$^c$CF$^d$CF$_2$O$^e$CF$_2$$^f$CF$_2$SO$_2$N$_3$; B=N$_3$$^g$ CF$_2$$^h$CFH$^i$CF$_2$O$^l$CF$_2$$^m$CF$_2$SO$_2$N$_3$ $^{19}$F-NMR; (CDCl$_3$; ppm): a: −89; b: −102; c: −185.4; d: −72.3; e: −79.3 (AB); f: −109.3; g: −78→−82 (m); h: −206 (J$^1$$_{H,F}$=48 hz); i: −74.5;→−83; l: −79.3 (AB); m: −109.3.

FT-IR (KBr; cm$^{-1}$): 1792 (CF$_2$=CF—CF$_2$ st.); 2163 (—N$_3$ st.); 1464+1384 (—SO$_2$—N$_3$ st.); 1200-1100 (CF st.).

Polymerization Runs

Polymerization Example 3—Polymerization of VDF/TrFE in the Presence of Monomer (Az2) (5% Moles)

In an AISI 316 steel up and over autoclave 46.2 ml of demineralized water were introduced. At room temperature, 3.38 g of sodium based micro emulsion obtained as described in Example 1 of U.S. Pat. No. 7,122,608 (SOLVAY SOLEXIS S.P.A.) 17 Oct. 2006, 0.55 g of monomer (Az2) of formula CF$_2$=CFCF$_2$OCF$_2$CF$_2$SO$_2$N$_3$ were then added, followed by 2.36 absolute bar of TrFE, 9.07 absolute bar of VDF which were metered from cylinders. Then, using a pump, 270 ml of a solution of ammonium peroxidisulphate (APS) diluted in water with a concentration of 0.1% in weight were fed to start polymerization. Then the temperature was brought to set-point temperature of 70° C., wherein pressure value in the autoclave was found to be 23.1 absolute bars.

Keeping constant the reaction temperature, the pressure was let to fall down to 14.2 abs bar. Then the reactor was cooled at room temperature, the latex was recovered and freezed for 48 hours and once unfreezed the so-coagulated polymer was washed with demineralized water and dried at 80° C. for 48 hours. 6.2 grams of polymer were obtained, whose nominal composition was as follows: VDF: 71.5% moles; TrFE: 23.5% moles; monomer (Az2): 5% moles.

Polymerization Example 4 of Comparison—Polymerization of VDF/TrFE in the Presence of Monomer (Az1) (10% Moles)

Same procedure as detailed in Polymerization Example 3 was followed except by using 1.1 g of monomer (Az1) of formula CF$_2$=CFOCF$_2$CF$_2$SO$_2$N$_3$ instead of monomer (Az2). Final pressure was about 0. 9.1 grams of polymer were obtained, whose nominal composition was as follows: VDF: 67.5% moles; TrFE: 21.5% moles; monomer (Az1): 10% moles.

Polymerization Example 5 of Comparison—Polymerization of VDF/TrFE in the Presence of Monomer (Az1) (5% Moles)

Similar procedure as in Polymerization Example 3 was followed, except by using 0.55 g of monomer (Az1) of formula CF$_2$=CFOCF$_2$CF$_2$SO$_2$N$_3$ instead of monomer (Az2), and setting set-point polymerization temperature at 105° C., and continuing polymerization 'till pressure fell to 4.2 abs bar. 9.6 g of polymer were obtained, whose nominal composition was as follows: VDF: 71.5% moles; TrFE: 23.5% moles; monomer (Az1): 5% moles.

Characterization of the Polymers of Examples 3 to 5C

The polymers obtained from Example 3 and Examples 4C and 5C were submitted to DSC analyses according to ASTM D3418 and to gel permeation chromatography for molecular weight determination. Results are detailed in table herein below.

TABLE 1

| Polymer | $T_g$ (° C.) | $T_{xx}$ (° C.) | $T_2$$^{Curie}$ (° C.) | $T_{2m}$ (° C.) | GPC Mp |
|---|---|---|---|---|---|
| From Ex. 3 | −6.0 | 66.2 | 93.5 | 110 | 59000 |
| From Ex. 4C | −23.3 | 60.6 | 91.8 | 91.8 | 28000 |
| From Ex. 5C | −24.2 | 70.4 | 108.6 | 108.6 | 34000 |

In above table, Tg is the glass transition temperature, $T_{xx}$ is the temperature of 1$^{st}$ crystallization, $T_{2m}$ is the 2$^{nd}$ melting temperature and $T_2$$^{Curie}$ is the Curie temperature as determined in 2$^{nd}$ heating cycle; Mp is the sequence molecular weight, as determined by GPC.

As it can be seen in above table, while polymerizing in strictly similar conditions, the VDF-TrFE polymer obtained using allyl sulfonazide monomer (Az2) according to the invention possesses a largely higher molecular weight over that achievable using corresponding vinyl sulfonazide monomer (Az1).

Manufacture of Films and Crosslinking Thereof Using Polymers of Examples 3 to 5C A) Spin Coating Specimens of the polymers obtained as detailed in Examples 3 to 5C, were dissolved in cyclopentanone so as to provide, after 3 hours stirring at a temperature of 40° C., clear solutions having a concentration of 8% in weight.

Said solutions were loaded into a Laurell WS-650 LITE SERIES spin coater and spin-coated at a speed of 2000 rpm onto glass substrates in order to obtain very thin polymeric layers on glass as substrates. The polymer layers so obtained were dried at 85° C. for 2 minutes. For each example, two polymeric films on glass were prepared.

All the samples obtained by the spin coating process, were all homogeneous, completely transparent and in the thickness range of 150-180 nm, as measured with Filmetrics F20 unit.

B) Crosslinking:

The polymer films obtained as above detailed were submitted to cross-linking procedures, either via thermal treatment or by UV treatment. Thermal treatment consisted in maintaining samples of films in a ventilated oven at a temperature of about 120 to 135° C.

For UV treatment, samples of films were passed through a semi automatic cross linker device, based on a UV lamp and equipped with a moving belt carrying the samples. Procedure was repeated so as to achieve the below detailed residence time under UV exposure.

In order to verify if the samples were crosslinked, pure acetone was poured on the films after treatment above: insolubility in such conditions was considered to be a clear evidence of suitable crosslinking. Results are summarized in the following table.

TABLE 2

| Polymer | From Ex. 3 | From Ex. 4C | From Ex. 5C |
|---|---|---|---|
| Film thickness (μm) | 160 | 175 | 168 |
| Solubility in acetone before any treatment | soluble | soluble | soluble |
| Crosslinking with thermal treatment Conditions: 130° C. during 20 minutes | | | |
| Solubility in acetone | insoluble | insoluble | soluble |
| Crosslinking with UV treatment Conditions: UV exposure for 4 seconds | | | |
| Solubility in acetone | insoluble | insoluble | soluble |

The table herein above well demonstrate the ability of the sulfonyl azide allylic monomer (Az2) of the invention in providing under adequate conditions crosslinking of the polymer matrix in which the same as hosted; comparison with Ex. 5C, comprising comparable amount of vinyl-type monomer (Az1), also shows that in this latter case no crosslinking is achieved, a larger amount of vinyl monomer being needed for achieving effective crosslinking (see Ex. 4C).

Determination of Ferroelectric Properties by P-E Hysteresis Loop

Specimens having dimensions 4 cm×4 cm were cut off from the spin-coated films obtained as above detailed from polymer of Ex. 3 and of Ex. 5C.

Figure 1:
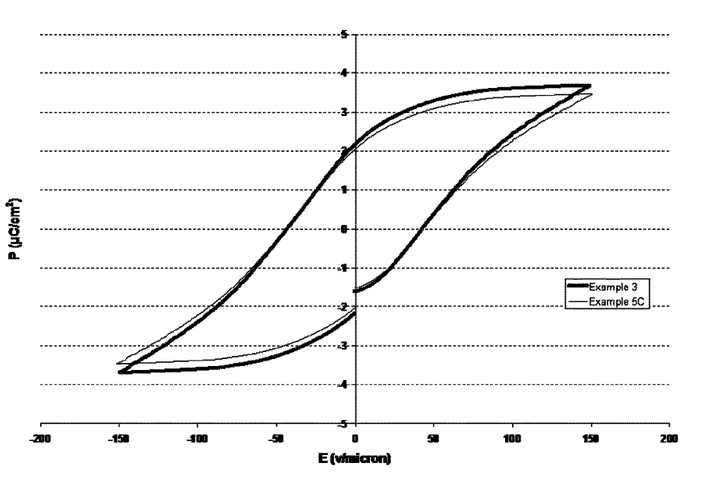
FIG. 1 is a plot of the P-E hysteresis curves for films obtained from inventive polymer of Example 3 and for polymer of Comparative Example 5, as measured by a Ferroelectric Radiant Equipment using an applied equivalent voltage of 150 v/micron with a bipolar drive.

A silver layer was deposited on said specimens in order to have a total electrode area of 7 cm² and providing a better electrical conductivity. Before the test, each sample was cured and then annealed at temperature of 130° C. for two hours in order to increase the polymer crystallinity. P-E hysteresis curves were recorded by means of a Ferroelectric Radiant Equipment (Precision II) using an applied equivalent voltage of 150 v/micron with a bipolar drive, with a precision of +3-5%. The plot of the recorded hysteresis curves is provided in FIG. 1 while Table 3 herein below summarizes some critical data.

TABLE 3

| Example | $P_{Max}$ (μC/cm²) | $P_r$ (μC/cm²) |
|---|---|---|
| 5C | 3.46 | 2.05 |
| 3 | 3.68 | 2.16 |

The table herein above well demonstrate the ability of the sulfonyl azide allylic monomer (Az2) of the invention in providing substantially analogous ferroelectric properties as those achieved in polymer of Ex. 5C, comprising comparable amount of vinyl-type monomer (Az1).

The invention claimed is:

1. A sulfonyl azide allylic monomer of formula (I):

$CF_2=CF-CF_2-O-R_f-SO_2N_3$     (I)

wherein $R_f$ is a divalent (per)fluorinated group, optionally comprising one or more than one ethereal oxygen atom.

2. The monomer of claim 1, wherein said monomer is a monomer of formula (Ia):

$CF_2=CF-CF_2-O-CF_2-R_f'-SO_2N_3$     (Ia), wherein $R_f'$ is a divalent $C_1$-$C_{12}$ (per)fluorinated group, optionally comprising one or more than one ethereal oxygen atom.

3. The monomer of claim 2, wherein said monomer is a monomer of formula (Ib):

$CF_2=CF-CF_2-O-CF_2-CF_2-SO_2N_3$     (Ib).

4. A process for the manufacture of a monomer of claim 1, comprising reacting a fluorosulfonic precursor of formula (II):

$CF_2=CF-CF_2-O-R_f-SO_2F$     (II)

wherein $R_f$ is a divalent (per)fluorinated group, optionally comprising one or more than one ethereal oxygen atom, with an azide salt.

5. A fluoropolymer (F) comprising recurring units derived from at least one monomer of formula (I):

$CF_2=CF-CF_2-O-R_f-SO_2N_3$     (I)

wherein $R_f$ is a divalent (per)fluorinated group, optionally comprising one or more than one ethereal oxygen atom, and, optionally, recurring units derived from at least one ethylenically unsaturated fluorinated monomer different from monomers of formula (I) and/or recurring units derived from an ethylenically unsaturated non-fluorinated monomer.

6. The fluoropolymer (F) according to claim 5, said fluoropolymer (F) comprising recurring units derived from at least one monomer of formula (I), and recurring units derived from vinylidene fluoride (VDF).

7. The fluoropolymer (F) according to claim 5, said fluoropolymer (F) comprising recurring units derived from vinylidene fluoride (VDF) and 10 to 50% by moles, of recurring units derived from trifluoroethylene (TrFE).

8. The fluoropolymer (F) according to claim 7, said fluoropolymer (F) comprising recurring units derived from vinylidene fluoride (VDF) and 15 to 40% moles of recurring units derived from trifluoroethylene (TrFE).

9. A process for the manufacture of the fluoropolymer (F) of claim 5, comprising polymerizing in the presence of a radical initiator at least one sulfonyl azide allylic monomer of formula (I):

$CF_2=CF-CF_2-O-R_f-SO_2N_3$     (I)

wherein $R_f$ is a divalent (per)fluorinated group, optionally comprising one or more than one ethereal oxygen atom, and optionally, at least one ethylenically unsaturated fluorinated monomer different from monomers of formula (I) and/or at least one ethylenically unsaturated non-fluorinated monomer.

10. A crosslinkable composition (CC) comprising the fluoropolymer (F) according to claim 5 and at least one curing agent in an amount of between 0.5% and 10% by weight relative to fluoropolymer (F).

11. The crosslinkable composition (CC) of claim 10, further comprising at least one curing agent selected from the group consisting of:

polyallyl derivatives comprising more than one ethylenically unsaturated allylic double bond;

polyvinyl derivatives comprising more than one ethylenically unsaturated vinyl double bond;

bis-olefin [bis-olefin (OF)] having general formula:

wherein $R_1$, $R_2$, $R_3$, $R_4$, $R_5$ and $R_6$, equal or different from each other, are H or $C_1$-$C_5$ alkyl; Z is a group of formula —$(O)_{e1}$-E-$(O)_{e2}$-, wherein e1 and e2, equal to or different from each other are independently 1 or 0, and E is a divalent $C_1$-$C_{18}$ group, optionally containing oxygen atoms, optionally at least partially fluorinated;

triazines substituted with ethylenically unsaturated groups; and polyazide compounds comprising more than one azide group.

12. The crosslinkable composition (CC) of claim 10, wherein the curing agent is present in an amount of between 1% and 7% by weight relative to fluoropolymer (F).

13. The crosslinkable composition (CC) of claim 11, wherein the polyallyl derivative comprising more than one ethylenically unsaturated allylic double bond is selected from triallyl cyanurate, triallyl isocyanurate (TAIC), tris(diallylamine)-s-triazine, triallyl phosphite, N,N-diallylacrylamide, N,N,N',N'-tetraallylmalonamide and mixtures thereof.

14. The crosslinkable composition (CC) of claim 11, wherein the polyvinyl derivative comprising more than one ethylenically unsaturated vinyl double bond is selected from trivinyl isocyanurate, 2,4,6-trivinyl methyltrisiloxane and mixtures thereof.

15. The crosslinkable composition (CC) of claim 11, wherein the polyazide compound comprising more than one azide group is at least one diazide selected from diazides of formula:

wherein each of j and j', equal to or different from each other, is 0 or an integer of 1 to 3, provided that j+j' is of at least 2, each of sd and sd', equal to or different from each other is independently 0 or 1, each of qd and qd', equal to or different from each other is independently 1 or 2, and $J_d$ is a (hydro)(fluoro)carbon group, optionally containing oxygen atoms, optionally at least partially fluorinated.

16. A method of forming a cured article, the method comprising crosslinking the fluoropolymer (F) according to claim 5, such that a cured article is formed.

17. A method for manufacturing an electrical or electronic device, the method comprising processing the fluoropolymer (F) of claim 5, and crosslinking the processed fluoropolymer (F).

18. The method of claim 17, wherein processing is effected by a solution processing technique selected from the group consisting of ink printing, casting, lithographic process.

19. A method of forming a cured article, the method comprising crosslinking the crosslinkable composition (CC) according to claim 10, such that a cured article is formed.

20. A method for manufacturing an electrical or electronic device, the method comprising processing the crosslinkable composition (CC) according to claim 10, and crosslinking the processed crosslinkable composition (CC).

* * * * *